United States Patent [19]

Nowotny

[11] 4,323,561
[45] Apr. 6, 1982

[54] PROCESS OF ENHANCING IMMMUNOGENIC RESPONSE IN MAMMALS BY THE ADMINISTRATION OF SYNTHETIC GLYCOLIPID ADJUVANTS

[75] Inventor: Alois H. Nowotny, Abington, Pa.

[73] Assignee: Temple University of the Commonwealth System of Higher Education, Philadelphia, Pa.

[21] Appl. No.: 830,681

[22] Filed: Sep. 6, 1977

[51] Int. Cl.$^3$ .......................... A61K 31/70; C07H 5/06
[52] U.S. Cl. ..................................... 424/180; 424/92; 536/18; 536/53
[58] Field of Search ................... 424/180, 92; 536/18, 536/53

[56] References Cited

U.S. PATENT DOCUMENTS 3,697,652  10/1972  Rovati et al. ......................... 536/18
3,934,009   1/1976  Gey et al. ............................. 536/53

Primary Examiner—Johnnie R. Brown

[57] ABSTRACT

A process is described for enhancing the immunogenic response of mammals. N-acylated-D-glucosamines were administered parenterally in the form of liposomes to mice at or before the time of administration of an immunogen or radiation, with the result that comparable or superior enhancement of the immune response was observed for these glycolipids when compared to LPS in assays measuring anti-SRBC or HGG hemagglutinin titers. The radiation protective effect of some of the synthetic adjuvants gave a definite protection, with up to 40% of lethally irradiated mice (700 R) surviving.

4 Claims, No Drawings

PROCESS OF ENHANCING IMMMUNOGENIC RESPONSE IN MAMMALS BY THE ADMINISTRATION OF SYNTHETIC GLYCOLIPID ADJUVANTS

BRIEF SUMMARY OF THE INVENTION

This invention relates to a process of enhancing immunogenic response in mammals. More particularly it relates to a process of enhancing the immunogenic response in mammals by the administration of a synthetic glycolipid adjuvant not later than the time of administration of an immunogenic agent.

Although the complete structure of endotoxic lipopolysaccharide (LPS) is not known, some salient features have been detected. The most unusual structural property is in the liquid moiety of the LPS, which has a phosphorylated D-glucosamine backbone, and this backbone has ester- and amide-bound long-chain carboxylic acids, thus forming a new class of glycolipids which has been named phosphomucolipid (1,2). The long-chain carboxylic acids of the lipid moiety were first studied by reversed phase paper chromatography and it was found that a hydroxy-acid, probably 3-hydroxymyristic acid, is one of the major components (3). These findings were confirmed by several laboratories and many further details were investigated (4–9).

During our efforts to synthesize model compounds structurally similar to known parts of the lipid moiety of endotoxic LPS, we prepared, among others, N-acylated D-glucosamine derivatives. One of the compounds, N-palmitoyl-D-glucosamine, was found by us to be active in B cell mitogenesis, although it is inactive in a number of characteristic endotoxicity reactions, such as mouse lethality, Limulus lysate clotting assay, pyrogenicity, and local Shwartzman skin assay in rabbits (10).

As a logical next step, homologs such as N-octanoyl-(NOG), N-decanoyl-(NDG), N-lauroyl-(NLG), N-myristoyl-(NMG), N-oleyl-(NOLG), and N-stearoyl-(NSG) D-glucosamines were prepared.

We have now found that the administation of N-acylated D-glucosamine compounds not later than the time of administration of an immunogen to a mammel enhances the immunogenic response of the mammal.

DETAILED DESCRIPTION OF THE INVENTION

Synthesis of N-acylated D-glucosamine derivatives

The procedure of Fieser et al (12) was followed. Ten mMole acid chloride (caprylyl, capryl, lauroyl, myristoyl, palmitoyl, oleyl, or stearoyl chloride) dissolved in 10 ml tetrahydrofuran were added dropwise to 10 mMole D-glucosamine.HCl dissolved in 20 ml 10% $Na_2CO_3$ solution under constant stirring at room temperature. The stirring was continued for 60 min, then 10 volumes of water were added. The white precipitate was filtered on a Buchner funnel and recrystallized twice from 50% hot propanol. The preparations were analyzed for C, H, and N, and their melting points were determined.

Endotoxic LPS preparation

LPS were isolated from Serratia marcescens 08 by the Boivin procedure, as modified earlier (13).

Preparation of liposomes from synthetic glycolipids

Two milligrams of the synthetic glycolipid were dissolved in 20 ml ethanol by refluxing in a 500-ml round bottom flask for 30 min in a water bath. With a rotating vacuum distillation apparatus such as the Buchi type (made in Switzerland), the alcohol was slowly removed while the flask was rotating in a warm water bath. Upon complete removal of ethanol, the glycolipid will form a thin layer on the inside wall of the 500-ml flask. The flask was briefly chilled in an ice bath before the addition of 20 ml double distilled water, followed by vigorous shaking for several minutes. The suspension was sonicated for 2 min at 1.7 amp. in a 50-ml beaker. At this time a droplet of this suspension placed under a light microscope will reveal the presence of liposomes as small spherical bodies. After a dry weight determination, the suspension was adjusted to a final concentration of 50 µg/ml.

Application of liposomal glycolipid suspension for enhancement of anti-SRBC response Washed SRBC were brought to a final concentration of $5 \times 10^7$ SRBC/ml in a 1.8% NaCl solution. Equal volumes of the SRBC and liposome suspensions were gently mixed to obtain isotonicity. This mixture was allowed to incubate, with occasional careful shaking, at room temperature for 30 min. Four-to 6-week old female ICR mice were used throughout these experiments. A total of 0.4 ml, containing $1 \times 10^7$ SRBC and 10 µg liposomes was injected i.p. per mouse.

Application of liposomal glycolipid suspension for enhancement of anti-HGG response Lyophilized HGG (Pentex Cohn fraction II) was slowly dissolved in a 1.8% pH adjusted (7.4) NaCl solution with minimal agitation to a final concentration of 1 mg/ml. Equal volumes of the HGG solution and the liposomal suspension were combined and allowed to incubate for 30 min, as described above. Each mouse was injected i.p. with a total volume of 0.4 ml containing 0.2 mg HGG and 10 µg liposomes in an isotonic NaCl solution.

Use of LPS for enhancement of anti-SRBC and anti-HGG response

The same procedure was followed as described above by replacing the equivalent concentration of glycolipid with distilled water-dissolved LPS.

Assays in the determination of adjuvancy

Spleen cell rosetts formation (RFC), plaque formation (PFC), and hemagglutination (HA) were carried out for the determination of the immune response to SRBC. The passive hemagglutination (PHA) assay was employed for the serum titer determination of the anti-HGG immunoglobulins. For all assays, pooled anti-sera and spleen cell suspensions were obtained from individual groups of six mice.

RFC assay

The method of Zaalberg (14) was used for RFC determination with the following modifications. Ten days after immunization and/or treatment, a spleen cell suspension was obtained by means of a tissue grinder containing 2 ml per spleen of Hanks' balanced salt solution (HBSS) and adjusted to pH 7.2 with $NaHCO_3$. After the cell suspension was passed through gauze and the cells were washed twice with HBSS, the cell suspension was adjusted to a concentration of $6 \times 10^7$ cells/ml. From these pooled spleen cell suspensions, triplicate samples of 100 μl were added to 100 μl of washed SRBC suspension (approximately $3 \times 10^7$ cells) in saline, pH 7.2. To each of these samples, 0.8 ml HBSS was added to bring the final volume to 1.0 ml. The samples were thoroughly agitated for 1 min by means of a Vortex before incubation at 4° C. for 3 hr. The test tubes containing the samples were gently rotated and handshaken to ensure a homogeneous cell suspension with minimum stress before analysis in a hemocytometer. Lymphocytes with more than five attached SRBC were classified as rosettes.

PFC assay

A modified technique of the hemolytic plaque assay first described by Jerne and Nordin (15) was used. Pooled, washed spleen cells from mice 4 days after immunization were obtained as described above. Appropriate cell suspensions (by volume: 1:10, 1:100, 1:500) were obtained for plating. However, accurate cell concentrations were determined for each sample by counting stained cells (Turk's stain) with a hemocytometer. To individual test tubes containing 2-ml aliquots of a 1% noble agar solution kept in liquid state at 50° C. in a water bath, the following were added: (1) 0.1 ml DEAE dextran (1%); (2) 0.1 ml 20% washed SRBC suspended in saline; (3) 0.1 ml of any of the various spleen cell concentrations. The contents of the tubes were quickly swirled and evenly layered onto the previously prepared base layer plates containing 15 ml 1.4% noble agar in HBSS. The plates were incubated for 1 hr. before guinea pig complement (Cappel Labs., State College, Pa.) was added. Incubation was continued for 30 min. At this time the complement was decanted and the plates were ready to be analyzed. Plates for each of the three concentrations of spleen cells were done in triplicate and analyzed randomly in a blind manner.

Direct HA and PHA

For direct HA, the procedure using the micro-titer system was used. Pooled anti-SRBC serum was obtained by heart puncture 10 days after treatment. The micro-titer system was also used for the PHA assay involving tannic acid-treated SRBC coated with HGG. The procedure followed was that of Boyden (16, 17).

Determination of endotoxicity

Shwartzman skin assays were carried out in albino rabbits by earlier described routine procedures (17). Chick embryo lethality was done on 11-day-old embryos and the preparations to be tested were given i.v., according to the method of Smith and Thomas (18). Mortality was recorded 24 hr. later and the $LD_{50}$ was calculated. The Limulus lysate assay was performed by the procedure of Levin et al. (19).

Protection from lethal irradiation

Mice in groups of 10 were irradiated with a total exposure dose of 700 R in individual perforated plastic centrifuge tubes mounted on a plywood rotating platform to ensure uniform exposure. The radiation source was a General Electric Maxitron 300 x-ray machine, operated at 20 ma, 300 Kvp, with added filtration of 0.26 mm Cu and 1.05 mm Al, yielding a half-value layer of 1.10 mm Cu. At a target distance of 60 cm, the air exposure dose rate was 235 R per minute as determined by a Victoreen air ionization chamber (model 154).

Glycolipid synthesis

The chemical synthesis of the glycolipids gave an approximately 50 to 65% yield of the calculated, measuring the amount of twice recrystallized products. The C, H, and N analyses were carried out by Micro-Analysis, Inc., laboratories, Wilmington, Del. 19808. Table I gives the results of these microanalyses as well as the melting point determinations. The close agreement between the theoretical and empirical values indicate the high degree of purity of the synthetic glycolipids.

Adjuvant effect of synthetic glycolipids and LPS on the anti-SRBC response

Before investigating the possible adjuvant properties of the liposomal glycolipids, we established the effect of the antigenic dose and its influence on the immune response enhancement by LPS, a known adjuvant. Table II shows the PFC response of normal and LPS-treated mice for increasing doses of SRBC. A better than 20-fold increase in the number of PFC was observed for the LPS-treated group receiving $5 \times 10^6$ SRBC. This observation is in agreement with those of Sjoberg et al. (20), who observed endotoxic adjuvancy only for low immunogenic doses of SRBC. In view of the low PFC response for the control group at this antigenic dose level, the antigenic dose of $1 \times 10^7$ SRBC was chosen for all the adjuvant determinations of the subseqent experiments.

The number of plaque-forming or antibody-producing cells in response to $1 \times 10^7$ SRBC/mouse was significantly enhanced for all the treated groups, except for the group treated with NDG. Similarly, a quantitative enhancement in serum anti-SRBC antibody levels was observed for the glycolypids and LPS relative to the control (Table III). In contrast to the PFC and serum antibody response, both clearly involving the B cell, the RFC response is thought to involve the T cell (Wilson, 21). Although all the glycolipids tested gave various degrees of enhancement, LPS was clearly the strongest adjuvant involving the resetting cell (Table IV).

Adjuvancy of the anti-HGG response

Our investigations of the effects of synthetic glycolipids and endotoxin on the antibody response to a serum protein, HGG, by means of PHA, demonstrated a low but significant enhancement of antibody titer for LPS and at least two of the glycolipids (NLG and NOLG). The results are summarized in Table IV.

Endotoxic reactions of the glycolipids

In the Shwartzman skinn assay, none of the preparations gave a positive response at the 50 μg level, but 2.5 μg endotoxin gave clearly detectable hemmorrhage in the skin of the rabbits. In chick embryo lethality of the synthetic glycolipids, none of them killed more than 20% at a 10-μg dose level given i.v. By way of comparison, the $LD_{50}$ of endotoxin in the same assay was found to be 0.006 μg. The Limulus lysate clotting assay was the only one that showed a slight activity by NPG and NSG preparations. According to the findings, these two preparations were $10^4$ and $10^5$ times less active than the control endotoxin preparation. Since this activity was maintained even after repeated recrystallization, one may exclude the possibility of endotoxin contamination.

Protection against lethal doses of radiation

In my copending application Ser. No. 659,423 filed Feb. 19, 1976, it is disclosed that endotoxin and its polysacchariderich fraction (PS) obtained from endotoxin by acid hydrolysis offered excellent to good radiation protection, respectively, when it preceded irradiation during specific time intervals (22). Treatment of mice 2 days before lethal irradiation exposure not only delayed the time of death but also increased the number of survivors to nearly the same degree as the PS for at least two of the glycolipids tested (Table V).

After several attempts to disperse the glycolipids mechanically or by solvent exchanges, the most consistent results were obtained by the procedure described here designed for the preparation of liposomes. This method gave not only a rather fine dispersion of the glycolipids, suitable for aqueous injection, but also significant adjuvant effects.

It should be emphasized that proper dispersion of the sample is absolutely essential for adjuvancy. Dispersions obtained by sonication at room or elevated temperatures, in the presence or absence of colloid stabilizers such as PS or proteins, yielded suspensions that appeared to be finely dispersed, but the adjuvant effect of these samples was marginal and for the most part not always reproducible. The possible reason for this may lie in the amorphous nature of the sonicated glycolipid aggregates. In the liposomes, the molecules are oriented and their even distribution on the surface of the spherical liposomes may present them in the most suitable way to obtain reproducible adjuvant effect.

The admixture of the glycolipid liposomes with the immunogen before injection is similarly important. In the case of both SRBC or HGG, a minimum of at least 30 min was found to be essential for elevated immune response. A reason for this time requirement has not been determined.

The proper dose of immunogen is also quite critical for the determination of adjuvant effect. A larger than optimal immunogenic dose of SRBC may result in an already high PFC or RFC response, which cannot be further augmented more than 1.5- or 2-fold with the best adjuvant. Similarly, the health of the mice is also a critical factor. If the animals are, or recently have been infected by some microorganism, their response in RFC may already be at a higher than normal level, most probably due to a nonspecific immunostimulation elicited by the infecting microbes. In such cases, hardly any adjuvant effect can be observed.

The immune response to $1 \times 10^7$ SRBC/mouse was clearly enhanced for nearly all treated groups, as expressed by the three separate assays involving anit-SRBC agglutination titer, PFC and RFC (Table III). Although the degree of adjuvancy in the three assays varied somewhat, it must be kept in mind that these assays represent a different stage and/or component of the immune response. The anti-SRBC serum obtained from mice 10 days after treatment/immunization most likely consists of a mixture of IgM and IgG antibodies, whereas the plaque formation seen 4 days after treatment/immunization is known to be an IgM response. Furthermore, although the PFC and serum antibody responses are known to involve the B cell, the RFC is thought to involve the T cell (21).

In the experiments reported here, the adjuvant was given simultaneously with the immunogen. Studying the optimal conditions for endotoxin-induced adjuvant effect, we found that endotoxin given 10 to 13 days before SRBC gives a better RFC adjuvant effect than that given together with the immunogen. Endotoxin given 5 days before SRBC has a definite immunosuppressive effect on the RFC response.

TABLE I

Chemical analyses of the synthetic glycolipids

| Preparations | C Calculated % | C Found % | H Calculated % | H Found % | N Calculated % | N Found % | M.P. °C. |
|---|---|---|---|---|---|---|---|
| NOG | 55.04 | 54.92 | 8.91 | 8.80 | 4.59 | 4.60 | 193–197 |
| NDG | 55.61 | 57.66 | 9.38 | 9.25 | 4.20 | 4.04 | 194–196 |
| NLG | 59.77 | 59.74 | 9.76 | 9.68 | 3.88 | 3.83 | 190–191 |
| NMG | 61.65 | 61.64 | 10.10 | 10.01 | 3.60 | 3.59 | 195–197 |
| NPG | 63.26 | 63.31 | 10.38 | 10.26 | 3.35 | 3.45 | 202–204 |
| NSG | 64.66 | 64.63 | 10.64 | 10.55 | 3.14 | 3.11 | 192–194 |

TABLE II

Adjuvant effect of lipopolysaccharide (LPS) as a function of the antigenic dose (sheep red blood cell, SRBC) in the plaque-forming cell (PFC) response[a] in ICR mice

| Treatment | Antigenic Dose of SRBC | | | | |
|---|---|---|---|---|---|
| | $1 \times 10^6$ | $5 \times 10^6$ | $1 \times 10^7$ | $5 \times 10^7$ | $1 \times 10^8$ |
| Control | 4.07 ± 0.32 | 4.62 ± 0.49 | 54.62 ± 6.11 | 255.65 ± 16.19 | 503.88 ± 42.77 |
| LPS (10 μg) | 7.55 ± 0.49 | 95.33 ± 7.1 | 209.44 ± 14.22 | 881.66 ± 53.14 | 719.44 ± 41.38 |
| | (1.85 ± 0.19)[b] | (20.63 ± 2.66)[b] | (3.83 ± 0.50)[b] | (3.90 ± 0.36)[b] | (1.42 ± 0.16)[b] |

[a]PFC response is expressed in the number of PFC/$10^6$ spleen cells
[b]Adjuvant index. Values in parentheses indicate $\frac{\text{PFC in LPS treated mice}}{\text{PFC in control mice}}$ ± standard error

TABLE III

Adjuvant effect of various preparations on the anti-SRBC immune response of ICR mice

| Adjuvant Preparations | Assays | | |
|---|---|---|---|
| | HA[a] | PFC[b] | RFC[c] |
| NOG | $2^7$ | 1.8 | 1.7 |
| NDG | $2^6$ | 0.7 | 3.2 |
| NLG | $2^7$ | 6.3 | 3.1 |
| NMG | $2^5$ | 1.6 | 1.0 |
| NPG | $2^9$ | 2.4 | 6.0 |
| NOLG | $2^8$ | 1.3 | 6.4 |
| NSG | $2^6$ | 1.9 | 2.5 |
| LPS | $2^7$ | 8.2 | 11.0 |
| None | $2^4$ | 1.0[d] | 1.0[e] |

[a]Hemagglutination titer.
[b]Plaque-forming cells, adjuvant index.
[c]Rosette-forming cells, adjuvant index.
[d]Control PFC response: 42.3 ± 4.9 PFC/$10^6$ spleen cells.
[e]Control RFC response: 6.1 1.1 RFC/$10^3$ spleen cells.

TABLE IV

Adjuvant effect of various preparations on the anti-HGG immune response of BALB/c mice.

| Preparation | Passive Hemagglutination Titer |
|---|---|
| NOG | $2^0$ |
| NDG | $2^0$ |
| NLG | $2^5$ |
| NMG | $2^3$ |

TABLE IV-continued

Adjuvant effect of various preparations on the anti-HGG immune response of BALB/c mice.

| Preparation | Passive Hemagglutination Titer |
|---|---|
| NPG | $2^4$ |
| NOLG | $2^6$ |
| NSG | $2^3$ |
| LPS | $2^3$ |
| None | $2^1$ |

TABLE V

Survival of lethally irradiated[a] ICR female mice treated with: (1) LPS (*Serratia marcescens* 10 μg); (2) PS (*Serratia marcescens* 10 μg); (3) NDG (50 μg); (4) NLG (50 μg); (5) NMG (50 μg); (6) NPG (50 μg)

| Treatment | Percent Survivors after Irradiation | | | | | |
|---|---|---|---|---|---|---|
| | Day 1 | Day 6 | Day 12 | Day 18 | Day 24 | Day 30 |
| LPS | 100 | 90 | 80 | 80 | 80 | 80 |
| PS[b] | 100 | 70 | 50 | 50 | 40 | 40 |
| NDG | 100 | 90 | 60 | 40 | 40 | 40 |
| NLG | 100 | 90 | 30 | 10 | 10 | 10 |
| NMG | 100 | 90 | 40 | 40 | 40 | 40 |
| NPG | 100 | 90 | 50 | 30 | 20 | 20 |
| Control | 100 | 80 | 0 | | | |

[a]Radiation exposure (700 R whole-body) occurred 2 days after treatment.
[b]Polysaccharide-rich fraction obtained by acid hydrolysis of LPS (1N HCl, 30 min. 100° C.).

The synthetic glycolipids described had no activity in chick embryo lethality, Shwartzman skin assay, and Limulus lysate tests, which are characteristic as well as sensitive assays of endotoxicity. The absence of these activities rules out the possibility that the glycolipid preparations are active because they are contaminated with endotoxin. (Abbreviations used in this paper: CSF, colony stimulating factor; HA, hemagglutination; HBSS, Hanks; balances salt solution; HGG, human γ-globulin; NDG, N-decanoyl-D-glucosamine; NOG, N-octanoyl-D-glucosamine; NOLG, N-oleyl-D-glucosamine; NSG, N-stearol-D-glucosamine; PHA, passive hemagglutination; PS, polysaccharide-rich fraction of hydrolyzed lipopolysaccharide; RFC, rosette-forming cell.)

REFERENCES

1. Nowotny, A., 1961. Chemical structure of a phosphomucolipid and its occurrence in some strains of Salmonella. J.Am.Chem.Soc. 83:501.
2. Nowotny, A., S. Thomas, and O. Duron, 1963. Chemistry of firmly-bound cell-wall lipids in gram-negative bacteria. Biochem. Biophys. Acta 1:422.
3. Nowotny, A., O. Luderitz, and O. Westphal, 1958. The application of circular paper chromatography of long chain fatty acids for analysis of the bacterial lipopolysaccharides. Biochem. Zeitschrift 330:47.
4. Burton, A. J., and H. E. Carter, 1964. Purification and characterization of the Lipid A component of the lipopolysaccharides from Escherichia coli. Biochemistry 3:411.
5. Kasai, N., 1966. Chemical studies on the lipid component of endotoxin, with special emphasis on its relation to biological activities. Ann. N.Y.Acad. Sci. 133:486.
6. Adams, G. A., and P. P. Singh, 1970. The chemical constitution of lipid A from Serratia marcescens. Can. J.Biochem, 48:55.
7. Gmeiner, J., M. Simon, and O. Luderitz, 1971. The linkage of phosphate groups and of 2-keto-3-deoxyoctonate to the Lipid A component in a Salmonella minnesota lipopolysaccharide, Eur.J.Biochem. 21:355.
8. Rietschel, E. T., H. Gottert, O. Luderitz, and O. Westphal, 1972. Nature and linkages of the fatty acids present in the Lipid-A component of Salmonella lipopolysaccharides, Eur.J.Biochem. 28:116.
9. Luderitz, O., C. Galanos, V. Lehmann, M. Nurmingen, E. T. Rietschel, G. Rosenfelder, M. Simon, and O. Westphal, 1973. Lipid A, chemical structure and biological activity. J.Infect.Dis. 128:S17
10. Rosenstreich, D. L., J. Asselineau, S. E. Mergenhagen, and A. Nowotny, 1974. A synthetic glycolipid with B-cell mitogenic activity. J.Exp. Med. 140:1404.
11. Skidmore, B. J., J. M. Chiller, D. C. Morrison, and W. O. Weigle, 1975. Immunologic properties of bacteria lipopolysaccharide (LPS): Correlation between the mitogenic, adjuvant, and immunogenic activities, J. Immunol. 114:770.
12. Fieser, M., L. Fieser, E. Toromanoff, Y. Hirata, H. Heymann, M. Teft, S. Bhattacharya, 1956. Synthetic emulsifying agents, J.AM.Chem. Soc. 78:2825.
13. Nowotny, A., K. R. Cundy, N. J. Neale, A. M. Nowotny, R. Radvany, S. P. Thomas, and D. J. Tripodi, 1966. Relation of structure to function in bacterial O-antigens, IV. Fractionation of the components. Ann.N.Y. Acad. Sci. 133:586.
14. Zaalberg, O. B., 1964. A simple method for detecting single anitbody forming cells. Nature 202:1231.
15. Jerne, N. K., and A. A. Nordin, 1963. Plaque formation in arar by single antibody-producing cells. Science 140:405.
16. Boyden, S. V., 1951. The absorption of proteins on erythrocytes treated with tannic acid and subsequent hemagglutination by anti-protein sera. J.Exp. Med. 93:107.
17. Nowotny, A., 1969. Basic Exercises in Immunochemistry, Springer-Verlag, New York.
18. Smith, R. T. and L. Thomas, 1956. The lethal effect of endotoxins on the chick embryo. J.Exp. Med. 104:217.
19. Levin, J., T. E. Poore, N. P. Zauber, and R. S. Oser, 1970. Detection of endotoxin in the blood of patients with sepsis due to gram-negative bacteria. N.Engl. J.Med. 283:1313.
20. Sjoberg, O., J. Andersson, and G. Moller, 1972. Lipopolysaccharide can substitute for helper cells in the antibody response in vitro. Eur. J.Immunol. 2:326.
21. Wilson, J. D., 1971. The relationship of antibody-forming cells to rosette-forming cells. Immunology 21:233.
22. Nowotny, A., U. H. Behling, and H. L. Chang, 1975. Relation of structure to function in bacterial endotoxins, VIII. Biological activities in a polysaccharide-rich fraction. J.Immunol. 115:199.
23. Ng, A.-K., R. C. Butler, C.-L. H. Chen, and A. Nowotny, 1976. Relationship of structure to function in bacterial endotoxins. IX. Differences in the lipid moiety of endotoxic glycolipids. J. Bacteriol. 126:511.
24. Nowotny, A., 1969. Molecular aspects of endotoxic reactions, Bacteriol. Rev. 33:72.
25. Radvany, R., N. L. Neale, and A. Nowotny, 1966. Relation of structure to function in bacterial O-antigens. VI. Neutralization of endotoxic O-antigens by hemologous O-antibody. Ann. N.Y.Acad. Sci. 133:763.

Having thus described my invention, I claim:

1. The method of enhancing the immunogenic response of a mammal which comprises administering to a mammal parenterally before or at the time of administration of an immunogen a mixture of the immunogen and an effective amount of an N-acylated-D-glucosamine selected from the group consisting of N-lauroyl-D-glucosamine, N-myristoyl-D-glucosamine, N-stearoyl-D-glucosamine, N-palmitoyl-D-glucosamine, N-caprylyl-D-glucosamine and N-capryl-D-glucosamine.

2. The method of claim 1 wherein the N-acylated-D-glucosamine is in the form of a liposome.

3. The method of enhancing the survival of a mammal which comprises administering to a mammal parenterally before the administration of radiation an effective amount of an N-acylated-D-glucosamine selected from the group consisting of N-decanoyl-D-glucosamine, N-lauroyl-D-glucosamine, N-myristoyl-D-glucosamine, N-octanoyl-D-glucosamine, N-oleyl-D-glucosamine, N-stearoyl-D-glucosamine, N-palmitoyl-D-glucosamine, N-caprylyl-D-glucosamine and N-capryl-D-glucosamine.

4. The method of claim 3 wherein the N-acylated-D-glucosamine is in the form of a liposome.

UNITED STATES PATENT OFFICE
CERTIFICATE OF CORRECTION

Patent No. 4,323,561            Dated April 6, 1982

Inventor(s) Alois Nowotny

It is certified that error appears in the above-identified patent and that said Letters Patent are hereby corrected as shown below:

Column 1, line 17 "liquid" should be --lipid--

Column 4, line 43 "resetting" should be --rosetting--

Column 5, line 64 "anit" should be --anti--

Signed and Sealed this

Sixteenth Day of November 1982

[SEAL]

Attest:

Attesting Officer

GERALD J. MOSSINGHOFF

Commissioner of Patents and Trademarks